United States Patent [19]

Hamilton

[11] 4,007,086

[45] Feb. 8, 1977

[54] INTERFERON INDUCTION
[75] Inventor: Ramon D. Hamilton, Portage, Mich.
[73] Assignee: The Upjohn Company, Kalamazoo, Mich.
[22] Filed: Jan. 23, 1975
[21] Appl. No.: 543,508
[52] U.S. Cl. .............................. 195/1.8; 204/160.1; 424/85
[51] Int. Cl.$^2$ ....................... C12K 9/00; B01J 1/10; A61K 45/02
[58] Field of Search .................. 424/85; 209/160.1; 195/1.8

[56] References Cited
OTHER PUBLICATIONS

Lindner–Frimmel J. Gen. Virol., vol. 25, pp. 147–150, 1974.
Mozes et al., J. Virology, vol. 13, pp. 646–651, Mar. 1974.
Coppey et al.–Chem. Abst., vol. 73 (1970), p. 107,625s.
Rosenquist et al.–Chem. Abst., vol. 67 (1967), p. 30945n.

*Primary Examiner*—Sam Rosen
*Attorney, Agent, or Firm*—William G. Jameson; Roman Saliwanchik

[57] ABSTRACT

An improved method for producing interferon which comprises irradiating interferon-producing human or animal cells in vitro with ultraviolet irradiation.

22 Claims, No Drawings

INTERFERON INDUCTION

BACKGROUND OF THE INVENTION

Interferon is the name given to certain protein molecules which appear in the blood or organs of animals, or in the medium of tissue cultures when such are exposed to an interferon inducer. Interferons are helpful in preventing or mitigating viral diseases. In seeking effective ways to induce interferon production, numerous investigations have been directed to agents and methods to induce interferon production. Such agents, which lead to the appearance of interferon in the blood or organs of animals, or in the medium of tissue cultures are designated as interferon inducers.

It has been previously shown that ultraviolet irradiation of cells prior to the addition of a viral inducer results in an inhibition of interferon production, see DeMaeyer-Quignard, J., and DeMaeyer, E., Inhibition of Interferon Synthesis and Stimulation of Virus Plaque Development in Mammalian Cell Cultures after Ultraviolet Irradiation, *Nature*, 205, 985 (1965) and Burke, D. C., and Morrison, J. M., Interferon Production in Chick Embryo Cells, *Virology*, 27, 108 (1965).

BRIEF SUMMARY OF THE INVENTION

This invention relates to an improvement in the art of interferon production. According to the present invention, interferon-producing human or animal cells are irradiated in vitro with from about 50 ergs/mm$^2$ to about 2500 ergs/mm$^2$ of ultraviolet irradiation prior to, concurrent with, or subsequent to the addition of a non-viral interferon inducer.

DETAILED DESCRIPTION OF THE INVENTION

This invention relates to an improvement in the art of non-viral-induced interferon production. More particularly, this invention relates to a method of enhancing the ability of interferon-producing human or animal cells to produce interferon in vitro by use of ultraviolet irradiation.

It has been unexpectedly found that irradiating interferon-producing human or animal cells with ultraviolet irradiation prior to, concurrent with, or subsequent to the addition of a non-viral interferon inducer enhances the yield of interferon. For example, irradiating interferon-producing human or animal cells with ultraviolet irradiation prior to, concurrent with, or subsequent to the addition of an inducing-effective amount of polyriboinosinic-polyribocytidylic acid complex enhances the yield of interferon. This is particularly surprising since heretofore it has been shown that ultraviolet irradiation of cells prior to the addition of a viral inducer results in an inhibition of interferon production, see DeMaeyer-Quignard, J., and DeMaeyer, E., Inhibition of Interferon Synthesis and Stimulation of Virus Plaque Development in Mammalian Cell Cultures after Ultraviolet Irradiation, *Nature* 205, 985 (1965) and Burke, D. C., and Morrison, J. M., Interferon Producing in Chick Embryo Cells, *Virology*, 27, 108 (1965).

It also has been found that the production of interferon by a given type of interferon-producing human or animal cell varies with the dose of ultraviolet irradiation and the timing of the application of the dose of ultraviolet irradiation relative to the addition of the polyriboinosinic-polyribocytidylic acid complex.

The term "interferon-producing human or animal cells" as used throughout the specification and claims means cells isolated from humans or animals, which cells are capable of being stimulated with a non-viral interferon inducer to produce interferon in vitro. Examples of such cells are cells isolated from embryos and fetuses, or from organs and tissues (such as foreskin, amnion, kidney, thyroid), leucocytes, various cell strains such as the human diploid cell strain known to the art as WI-38, and transformed cell lines such as Hela.

The term in vitro used throughout the specification means cells isolated, grown or treated as stationary cultures (e.g., tissue culture dishes), as non-stationary cultures (e.g., roller bottles and microcarriers), or as suspensions.

The term "non-viral interferon inducer" as used throughout the specification and claims means all non-viral agents which can be used to induce the production of interferon in interferon-producing human or animal cells. Examples of such agents are endotoxins, bacteria, trachoma-inclusion conjunctivitis (TRIC) agents, mycoplasmas, protozoa, rickettsiae, synthetic chemical polymers, mitogens, polysaccharides, antibiotics, low-molecular weight interferon inducers such as tilorone hydrochloride, natural and synthetic nucleic acids including single and double-stranded ribonucleic acids and complexes thereof with polysaccharides and other substances.

The term "polynucleotide" as used throughout the specification and claims means all polynucleotides which can be used to induce the production of interferon in interferon-producing human or animal cells. The term polynucleotide includes double-stranded ribonucleic acids and complexes thereof with polysaccharides and other substances. Such double-stranded ribonucleic acids include polyriboguanylic-polyribocytidylic acid complex (poly G:C), polyriboinosinic-polyribocytidylic acid complex (poly I:C), polyriboadenylic-polyribouridylic acid complex (poly A:U), and the like. A comprehensive disclosure of such inducers is given in Finter, *Interferons and Interferon Inducers* (1973).

The term "polyriboinosinic-polyribocytidylic acid complex" as used throughout the specification and claims means the synthetic double-stranded ribonucleic acid commonly referred to in the art as poly rI:rC, poly I:C, or poly I:poly C.

The present invention relates to an improvement in the method of producing interferon in vitro which consists of inducing interferon-producing human or animal cells with an inducing-effective amount of a non-viral interferon inducer, said improvement comprising irradiating the cells with from about 50 ergs/mm$^2$ to about 2500 ergs/mm$^2$, preferably about 100 ergs/mm$^2$ to about 1000 ergs/mm$^2$ of ultraviolet irradiation prior to, concurrent with, or subsequent to the addition of the non-viral interferon inducer.

The non-viral interferon inducer can be any non-viral interferon inducer capable of inducing the particular human or animal cells to produce interferon.

An embodiment of this invention relates to an improvement in the method of producing interferon in vitro which consists of inducing interferon-producing human or animal cells with an inducing-effective amount of a polyribonucleotide; said improvement comprising irradiating the cells with from about 50 ergs/mm$^2$ to about 2500 ergs/mm$^2$, preferably about 100 ergs/mm² to about 1000 ergs/mm², of ultraviolet irradiation prior to, concurrent with, or subsequent to the addition of the polyribonucleotide.

The polyribonucleotide can be any polyribonucleotide capable of inducing the particular human or animal cells to produce interferon.

A preferred embodiment of this invention relates to an improvement in the method of producing interferon in vitro which consists of inducing interferon-producing human or animal cells with an inducing-effective amount of polyriboinosinic-polyribocytidylic acid complex, said improvement comprising irradiating the cells with from about 50 ergs/mm² to about 2500 ergs/mm², preferably about 100 ergs/mm² to about 1000 ergs/mm², of ultraviolet irradiation prior to, concurrent with, or subsequent to the addition of the polyriboinosinic-polyribocytidylic acid complex.

To determine the dose of ultraviolet irradiation which can be used with a given type of human or animal cell capable of producing interferon, a curve representing the response in quantity of interferon produced as a function of the ultraviolet irradiation dose can first be prepared, and the optimum ultraviolet irradiation dose deduced therefrom. In determining the optimum dose of ultraviolet irradiation to be utilized, an arbitrary point in time for the application of the dose of ultraviolet irradiation relative to the addition of an inducing-effective amount of a non-viral interferon inducer can be used; preferably immediately prior to, concurrent with, or no more than 2 hours subsequent to the addition of the non-viral interferon inducer.

To determine the optimum point in time for application of the dose of ultraviolet irradiation relative to the addition of the inducing-effective amount of a nonviral interferon inducer, a curve representing the response in quantity of interferon produced as a function of the point in time of application can be prepared, and the optimum point in time of application of the dose of ultraviolet irradiation relative to the addition of the non-viral interferon inducer deduced therefrom.

Generally, the point in time for application of the dose of ultraviolet irradiation is from 8 hours prior to until about 4 hours subsequent to, including concurrent with, the addition of the non-viral interferon inducer. Preferably, the point in time for application of the dose of ultraviolet irradiation is from immediately before to 2 hours subsequent to the addition of the nonviral interferon inducer.

A source of ultraviolet irradiation which can be employed is a "*Westinghouse*" G15T8 Sterilamp which produces about 44–50 ergs/mm²/sec. at a distance of 30 cm. and has a maximum emission of ultraviolet irradiation with the wavelength of 2537 A. However, any source of ultraviolet irradiation, preferably of a similar wavelength, can be used. Thus, the type of lamp or other device used as a source of ultraviolet irradiation is not critical.

The various media and other details of interferon induction with a non-viral interferon inducer are well known to the art, see, e.g., Finter, *Interferons and Interferon Inducers* (1973) and references cited therein.

Subsequent to the invention described herein, it has been reported that ultraviolet irradiation of rabbit kidney cells prior to their exposure to polyinosinate-polycytidylate (poly[I]:poly[C]) results in enhanced production of interferon, see Mozes, L., and Vilcek, J., Interferon Induction in Rabbit Cells Irradiated with UV Light, *Journal of Virology*, 13, 646 (1974). It has also been reported, subsequent to the invention described herein, that polyinosinate-polycytidylate (poly I:poly C)-induced interferon production in cultures of human foreskin fibroblast strains was increased by UV-irradiation of cells at the time of exposure to inducer or at 2 hours after induction; and incubation of cells with interferon prior to induction (priming) and UV-irradiation exerted a cooperative enhancing effective on interferon production, see Mozes, L. et al., Increased Interferon Production in Human Cells Irradiated with Ultraviolet Light, *Interferon Scientific Memoranda*, Memo I-A62/1, August, 1974. It has also been reported, subsequent to the invention described herein, that UV-irradiation of human diploid cells enhanced interferon production after induction with poly I:C; and interferon production was further increased by DEAE-dextran in cultures already enhanced by U.V., see, S. J. Lindner-Frimmel, *Enhanced Production of Human Interferon by U.V. Irradiated Cells*, J. Gen. Virol. (1974), 25, 147–150.

The following examples are given merely as illustrations of the present invention and are not to be construed as limiting the scope of the invention.

The term "MEM" as used in the following examples means Minimum Essential Medium Eagles Earle's Base), Baltimore Biological Company, Baltimore, Md. The components of MEM are:

| Components | mg./liter |
| --- | --- |
| AMINO ACIDS | |
| L-Arginine HCl | 126.4 |
| L-Cystine | 24.0 |
| L-Glutamine | 292.0 |
| L-Histidine HCl.H$_2$O | 41.9 |
| L-Isoleucine | 52.5 |
| L-Leucine | 52.4 |
| L-Lysine HCl | 73.1 |
| L-Methionine | 14.9 |
| L-Phenylalanine | 33.0 |
| L-Threonine | 47.6 |
| L-Tryptophan | 10.2 |
| L-Tyrosine | 36.2 |
| L-Valine | 46.8 |
| VITAMINS | |
| D-Ca-Pantothenate | 1.0 |
| Choline Chloride | 1.0 |
| Folic Acid | 1.0 |
| i-Inositol | 2.0 |
| Nicotinamide | 1.0 |
| Riboflavin | 0.1 |
| Thiamine HCl | 1.0 |
| Inorganic Salts and Other Components EARLE'S BSS | |
| CaCl$_2$.2H$_2$O | 265.0 |
| KCl | 400.0 |
| MgSO$_4$.7H$_2$O | 200.0 |
| NaCl | 6,800.0 |
| NaHCO$_3$ | 2,200.0 |
| NaH$_2$PO$_4$.H$_2$O | 140.0 |
| Dextrose | 1,000.0 |
| Phenol red | 10.0 |

The term "MEM-10" as used in the following examples means MEM supplemented with 10% sterile filtered fetal bovine serum, inactivated at 56° C. for 30 minutes, and 1.5 mg./ml. sodium bicarbonate. MEM-10 also contains 100 units sodium penicillin G, 100 mcg. streptomycin phosphate and 6 mcg. fungizone per ml.

The term "MEM-2" as used in the following examples means MEM supplemented with 2% sterile filtered fetal bovine serum, inactivated at 56° C. for 30 minutes, and 1.5 mg./ml. sodium bicarbonate. MEM-2 also contains 100 units sodium penicillin G, 100 mcg. streptomycin phosphate and 6 mcg. fungizone per ml.

The term "MEM-2A" as used in the following examples means MEM supplemented with 2% agamma calf serum, inactivated at 56° C. for 30 minutes, and 1.2 mg./ml. sodium bicarbonate. MEM-2A also contains 50 units sodium penicillin G and 50 mcg. streptomycin phosphate per ml.

The term "HBSS" as used in the following examples means Hanks' balanced salt solution supplemented with 50 units sodium penicillin G and 50 mcg. streptomycin phosphate per ml. The components of HBSS are:

| Components | mg./liter |
| --- | --- |
| NaCl | 8,000 |
| KCl | 400 |
| $CaCl_2 \cdot 2H_2O$ | 186 |
| $MgSO_4 \cdot 7H_2O$ | 200 |
| $Na_2HPO_4 \cdot 7H_2O$ | 90 |
| $KH_2PO_4$ | 60 |
| Dextrose | 1,000 |
| Phenol red | 20 |
| $NaHCO_3$ | 350 |

The term "Medium 199" as used in the following examples means Medium 199 (HBSS base), Baltimore Biological Company, Baltimore, Md. The components of Medium 199 are:

| Components | mg./liter |
| --- | --- |
| AMINO ACIDS | |
| L-Alanine | 25.0 |
| L-Arginine HCl | 70.0 |
| L-Aspartic acid | 30.0 |
| L-Cysteine HCl | 0.1 |
| L-Cystine | 20.0 |
| L-Glutamic acid | 67.0 |
| L-Glutamine | 100.0 |
| Glycine | 50.0 |
| L-Histidine $HCl \cdot H_2O$ | 22.0 |
| Hydroxy-L-proline | 10.0 |
| L-Isoleucine | 20.0 |
| L-Leucine | 60.0 |
| L-Lysine HCl | 70.0 |
| L-Methionine | 15.0 |
| L-Phenylalanine | 25.0 |
| L-Proline | 40.0 |
| L-Serine | 25.0 |
| L-Threonine | 30.0 |
| L-Tryptophan | 10.0 |
| L-Tyrosine | 40.0 |
| L-Valine | 25.0 |
| VITAMINS | |
| P-Aminobenzoic acid | 0.050 |
| Ascorbic acid | 0.050 |
| D-Biotin | 0.010 |
| Calciferol | 0.100 |
| D-Ca-Pantothenate | 0.010 |
| Cholesterol | 0.200 |
| Choline chloride | 0.500 |
| Folic acid | 0.010 |
| i-Inositol | 0.050 |
| Menadione | 0.010 |
| Nicotinamide | 0.025 |
| Nicotinic acid | 0.025 |
| Pyridoxal HCl | 0.025 |
| Pyridoxine HCl | 0.025 |
| Riboflavin | 0.010 |
| Thiamine HCl | 0.010 |
| DL-α-Tocopherolphosphate ($Na_2$) | 0.010 |
| Tween 80* | 5.000 |
| Vitamin A acetate | 0.140 |
| OTHER COMPONENTS | |
| Adenine $HCl \cdot 2H_2O$ | 12.10 |
| Adenosine-5'-monophosphoric acid, dihydrate (AMP) (Muscle adenylic acid) | 0.20 |
| Adenosine-5'-triphosphate disodium, tetrahydrate (ATP) | 1.08 |
| Deoxyribose | 0.50 |
| Dextrose | 1,000.00 |
| Glutathione (Reduced) | 0.05 |
| Guanine $HCl \cdot H_2O$ | 0.33 |
| Hypoxanthine | 0.30 |
| Phenol red | 20.00 |
| Ribose | 0.50 |
| Sodium acetate $\cdot 3H_2O$ | 83.00 |
| Thymine | 0.30 |
| Uracil | 0.30 |
| Xanthine | 0.34 |
| INORGANIC SALTS | |
| NaCl | 8,000.0 |
| KCl | 400.0 |
| $CaCl_2 \cdot 2H_2O$ | 186.0 |
| $MgSO_4 \cdot 7H_2O$ | 200.0 |
| $Na_2HPO_4 \cdot 7H_2O$ | 90.0 |
| $KH_2PO_4$ | 60.0 |
| $Fe(NO_3)_3 \cdot 9H_2O$ | 0.7 |
| $NaHCO_3$ | 350.0 |

*Trademark of Atlas Powder Company

The term "Medium 199 (1X)" as used in the following examples means Medium 199 supplemented with 5% sterile filtered fetal bovine serum, inactivated at 56° C. for 30 minutes, and 1.3 mg./ml. sodium bicarbonate. Medium 199 (1X) also contains 50 units sodium penicillin G and 50 mcg. streptomycin phosphate and 1 mcg. fungizone per ml.

The term "Medium 199 (1X) plaquing agar" as used in the following examples means Medium 199 (1X) containing 0.85 to 1% Noble agar.

The term "PBS" as used in the following examples means phosphate buffered saline, i.e., 1 ml. of heat sterilized 1M sodium phosphate (pH 7) is added per 100 ml. saline.

The term "Trypsin (PBS) solution" as used in the following examples means a 0.25% trypsin solution prepared by diluting a stock solution 1:20 in PBS. The stock solution is prepared by adding 9.5 ml. water to a 10 ml. vial of lyophilized Bacto trypsin.

The term "saline" as used in the following examples means physiological or isotonic saline, i.e., 0.9% sodium chloride solution.

All incubations in the following examples are at about 37° C. and are under an atmosphere of 5% carbon dioxide, unless otherwise specified.

A "Westinghouse" G15T8 Sterilamp which produces about 44–50 ergs/mm²/sec. at a distance of 30 cm. and has a maximum emission of ultraviolet irradiation with a wavelength of 2537 A is used as a source of ultraviolet irradiation in the following examples, unless otherwise specified.

The term "sheeted" as used in the following examples means when the cells are a confluent monolayer.

The term "plastic tissue culture plates" as used in the following examples means 60 mm. Falcon plastic tissue culture plates supplied by Falcon Plastic, Los Angeles, Cal., unless otherwise specified.

EXAMPLE 1

The term "assayed" as used herein means assayed with a virus plaque assay as follows:

Human foreskin fibroblasts (HFF), obtained by trypsinization of infant foreskin tissue as described herein, are seeded on day 1 on 60 mm. plastic tissue culture plates in 5 ml. MEM-10 growth medium, incubated, reach confluency on day 4 or 5 and are used on day 5.

The growth medium is removed and the plates are overlayed with 2 ml. Medium 199 (1X) and dilutions of the interferon sample in PBS (pH 7) are added to the plates in a volume of 0.1 to 0.2 ml. Control plates to which are added PBS alone, or an interferon standard in PBS, are also included in the assay. The plates are incubated for 16–24 hours and then aspirated and challenged with 40–80 pfu of vesicular stomatitis virus in 0.5 ml. HBSS. After 2 hours incubation the plates are overlayed with 5 ml. Medium 199 plaquing agar. The virus plaques are counted after 3–5 days' incubation.

Interferon concentrations are expressed as the reciprocal of the dilution producing a 50% reduction of virus plaques, as compared to a control without interferon.

One interferon unit is that amount of interferon that produces a 50% reduction of virus plaques, as compared to a control without interferon. In this example an international human reference interferon (69/19) has been included and, within the accuracy of the assay, the units expressed are equivalent to international units without correction.

Human foreskin fibroblasts (HFF) are obtained by trypsinization of infant foreskin tissue as follows:

Infant foreskin tissue is obtained at the time of circumcision. The time from birth to circumcision is about 2 days. The foreskin is cleansed by the physician, excised, washed with 10–20 ml. cold saline and transferred to 10–20 ml. cold MEM-10. The tissue is stored at 4° C. and processed within two hours after collection.

The tissue is washed 3 times with saline at room temperature and cut with scissors into 6–12 pieces which are collected in a 50 ml. screw-top flask containing a magnetic stirring bar. 7.5 Ml. of tryspin (HBSS) solution is added to the flask and the tissue is stirred at 37° C. for 15 minutes and then decanted through a double layer of cheesecloth to collect the undigested tissue. The filtrate is discarded and the tissue returned to the flask with 7.5 ml. fresh tryspin (HBSS) solution and digestion at 37° C. continued. After 1 hour the suspension is filtered again into 15 ml. ice cold MEM-10 and the filtrate saved. The undigested tissue is returned to the flask and digested a third time at 37° C. for 1 hour with 5 ml. trypsin (HBSS) solution, pooling this filtrate with the second. The cells, recovered by centrifugation for 5 minutes at 800 × g., are washed 1 time with a mixture of 3 ml. MEM-10 and 7 ml. HBSS and suspended in 15 ml. MEM-10 for culturing in an incubator under 5% $CO_2$ as a single aliquot on a plastic tissue culture plate 100 mm. × 20 mm. After 48 hours, and at 3 day intervals thereafter until sheeted, the culture is refed with 15 ml. MEM-10.

Cells from the primary plate, when sheeted, are split into two tissue culture bottles (75 cm²). For passage, plates or bottles are washed 2 times with saline and trypsinized 5 minutes at 37° C. with trypsin (PBS) solution. Removal of the cells from bottles is facilitated by rubber scrapers. Bottles are not incubated in a $CO_2$ incubator, but the $CO_2$ of the environment is increased as follows: to each bottle is added 12.5 ml. MEM-10 and 12.5 ml. "gassed" MEM-10 (prepared by bubbling 100% $CO_2$ through MEM-10 for 1 minute and the storing sealed) plus the cells in 1 or 2 ml. MEM-10.

After the first passage bottles are routinely passed by splitting 1:5 as described above. When sheeted (3 to 4 days) the bottles are aspirated and fed with 25 ml. MEM-2. Cells are refed with 25 ml. MEM-2 in 5 days and passed every 13–14 days.

From each tissue culture bottle (75 cm²) twenty 60 mm. plastic tissue culture plates are seeded (2.1 × 10⁵ cells per plate) for interferon production. The cells are seeded on the 60 mm. plates in 5 ml. MEM-10 growth medium.

Part A — Effect of Ultraviolet Irradiation on the Ability of Human Foreskin Fibroblasts to Produce Interferon Human foreskin fibroblasts (HFF), obtained by trypsinization of infant foreskin tissue as described above, are seeded on day 1 on 60 mm. plastic tissue culture plates in 5 ml. MEM-10 growth medium, incubated, and reach confluency on day 3 and are used on day 6 (6 × 10⁵ cells/plate). The growth medium is removed from six plates and the plates are washed 3 times with saline. One plate serving as a control is not irradiated and the remaining 5 plates are irradiated immediately (Westinghouse Sterilamp G15T8, 30 cm. working distance) for 1, 5, 10, 15 and 20 seconds, respectively. After irradiation the plates are overlayed with 2 ml. MEM-2A containing 10 mcg./ml. polyriboinosinic-polyribocytidylic acid complex (poly I:C) and incubated for 2 hours. The plates are washed 3 times with saline, given 2 ml. fresh MEM-2A and incubated 16½ hours.

Another portion of the plates (6) are overlayed with 2 ml. MEM-2A containing 10 mcg./ml. polyriboinosinic-polyribocytidylic acid complex (poly I:C) after removing the growth medium and incubated for 2 hours. The plates are washed 3 times with saline. One plate serving as a control is not irradiated and the remaining 5 plates are irradiated immediately (Westinghouse Sterilamp G15T8, 30 cm. working distance) for 1, 5, 10, 15 and 20 seconds, respectively. After irradiation the plates are overlayed with 2 ml. MEM-2A and incubated for 16½ hours.

The 16½ hour medium of the plates is assayed for interferon. The results are shown in Table 1.

TABLE 1

| UV Exposure | Dose poly I:C | Irradiated Before or After Induction | Interferon Yield units/plate |
|---|---|---|---|
| 0 seconds | 10 mcg./ml. | before | 20 |
| 1 " | " | " | 50 |
| 5 " | " | " | 280 |
| 10 " | " | " | 428 |
| 15 " | " | " | 414 |
| 20 " | " | " | 424 |
| 0 seconds | " | after | 20 |
| 1 " | " | " | 16 |
| 5 " | " | " | 194 |
| 10 " | " | " | 194 |
| 15 " | " | " | 780 |
| 20 " | " | " | 686 |
| 0 seconds | 100 mcg./ml. | after | 340 |
| 1 " | " | " | 320 |
| 5 " | " | " | 2098 |
| 10 " | " | " | 5132 |
| 15 " | " | " | 2876 |
| 20 " | " | " | 4344 |

Part B — Effect of Ultraviolet Irradiation on the Yields of Interferon Obtained from Human Foreskin Fibroblasts Induced with Various Doses of Polyriboinosinic-Polyribocytidylic Acid Complex Human foreskin fibroblasts (HFF), obtained by typsinization of infant foreskin tissue as described above, are seeded on day 1 on 60 mm. plastic tissue culture plates in 5 ml. MEM-10 growth medium, incubated, and used on day 5 as confluent cell sheets containing approximately 6 × $10^5$ cells/plate. The growth medium is removed from 3 plates and the plates are overlayed with 2 ml. MEM-2A containing 50 mcg./ml. polyriboinosinic-polyribocytidylic acid complex (poly I:C) and incubated for 2 hours. The plates are washed 3 times with saline. One plate serving as a control is not irradiated and the remaining 2 plates are irradiated immediately [Westinghouse Sterilamp G15T8, 30 cm. working distance, measured dose 50 ergs/mm$^2$/sec. (Blak-Ray Ultraviolet Intensity Meter)] for 15 seconds. After irradiation the plates are overlayed with 2 ml. MEM-2A and incubated for 7¾ hours. The medium is harvested and assayed for interferon. The plates are replenished with 2 ml. fresh MEM-2A and incubated for 8¼ hours. The medium is harvested again at 16 hours post-irradiation and assayed for interferon.

Using the procedure, above, interferon is similarly induced by substituting 2 ml. MEM-2A containing 100 and 200 mcg./ml. of polyriboinosinic-polyribocytidylic acid complex (poly I:C) for the 50 mcg./ml. used above.

The results are shown in Table 2.

TABLE 2

| UV Exposure | Dose poly I:C | Interferon Yield units/plate | | |
|---|---|---|---|---|
| | | 0–7¾ hr | 7¾–16 hr | Total |
| 0 seconds | 50 | 578 | 140 | 718 |
| 15 " | 50 | 2802* | 2866* | 5668* |
| 0 seconds | 100 | 1340 | 472 | 1812 |
| 15 " | 100 | 6078* | 6114* | 12192* |
| 0 seconds | 200 | 968 | 478 | 1446 |
| 15 " | 200 | 3218* | 7114* | 10332* |

*Average for 2 plates

Part C — The Effect of Varying Induction Time and Time of Ultraviolet Irradiation on the Yields of Interferon Obtained from Human Foreskin Fibroblasts Induced with Polyriboinosinic-Polyribocytidylic Acid Complex.

Human foreskin fibroblasts (HFF), obtained by trypsinization of infant foreskin tissue as described above, are seeded on day 1 on 60 mm. plastic tissue culture plates in 5 ml. MEM-10 growth medium, reach confluency on day 3 and are used on day 5. The growth medium is removed and the plates are overlayed with 2 ml. MEM-2A containing 100 mcg./ml. polyriboinosinic-polyribocytidylic acid complex (poly I:C). After the induction time indicated in Table 3, groups of 2 plates each are washed 3 times with saline and irradiated immediately [Westinghouse Sterilamp G15T8, 30 cm. working distance, measured dose 44 ergs/mm$^2$/sec. (Blak-Ray Ultraviolet Intensity Meter)] for 15 seconds or are washed 3 times, given 2 ml. MEM:2A, and irradiated, as above, after an incubation, as indicated in Table 3. After irradiation the plates are overlayed with 2 ml. MEM-2A and incubated.

The medium is harvested at 21 hours post irradiation and assayed, and the plates replenished with 2 ml. fresh MEM-2A and incubated for 24 hours. The medium is again harvested at 45 hours post-irradiation and assayed. The results are shown in Table 3.

TABLE 3

| Induced | Irradiated at: | Interferon Yield* (units/plate) | | |
|---|---|---|---|---|
| | | 21 hr Yield | 45 hr Yield | Total Yield |
| 0–2 hr | None (control) | 1654 | 92 | 1746 |
| 0–2 hr | 0 hr (before poly I:C) | 14420 | 4790 | 19210 |
| 0–2 hr | 2 hr | 16502 | 24444 | 40946 |
| 0–2 hr | 3 ¾ hr | 4634 | 2690 | 7324 |
| 0–3 hr | 3 hr | 4212 | 5326 | 9538 |
| 0–3 ¾ hr | 3 ¾ hr | 5164 | 1782 | 6946 |
| 0–15 min | 15 min | 18326 | 14044 | 32370 |
| 0–15 min | 2 hr | 23250 | 18234 | 41484 |
| 0–30 min | 30 min | 18100 | 16682 | 34782 |
| 0–1 hr | 1 hr | 24320 | 23722 | 48042 |

*Average for 2 plates

Part D — The Effect of Various Dosage Levels Ultraviolet Irradiation on Interferon Production by Human Foreskin Fibroblasts Irradiated After or Before Induction with Polyriboinosinic-polyribocytidylic Acid Complex (poly I:C)

Human foreskin fibroblasts (HFF), obtained by trypsinization of infant foreskin tissue as described above, are seeded on day 1 on 60 mm. plastic tissue culture plates in 5 MEM-10 growth medium, incubated, and reach confluency on day 3 and are used on day 5. The growth medium is removed and a portion of the plates are washed 1 time with saline. Two plates serving as a control are not irradiated and groups of 2 plates each are irradiated immediately [Westinghouse Sterilamp G15T8, 30 cm working distance, measured dose 44 ergs/mm$^2$/sec. (Blak-Ray Ultraviolet Intensity Meter)] for 2, 5, 10, 15, 20 and 30 seconds, respectively. After irradiation the plates are overlayed with 2 ml. MEM-2A containing 100 mcg./ml. polyriboinosinic-polyribocytidylic acid complex (poly I:C) and incubated for 2 hours. The medium from the plates is harvested at 21½ hours post-irradiation and assayed, and the plates replenish with 2 ml. fresh MEM-2A and incubated for 24 hours. The medium is harvested again at 45½ hours post-irradiation and assayed.

With another portion of plates, the growth medium is removed and the plates overlayed with 2 ml. MEM-2A containing 100 mcg./ml. polyriboinosinic-polyribocytidylic acid complex (poly I:C) and incubated for 2 hours. The plates are then washed 3 times with saline. Groups of 2 plates each are irradiated immediately [Westinghouse Sterilamp G15T8, 30 cm. working distance, measured dose 44 ergs/mm$^2$/sec. (Blak-Ray Ultraviolet Intensity Meter)] for 2, 5, 10, 15, 20 and 30 seconds, respectively. After irradiation the plates are overlayed with 2 ml. MEM-2A and incubated for 21½ hours post-irradiation. The medium is harvested and assayed. The plates are replenished with 2 ml. fresh MEM-2A and incubated for 24 hours. The medium is harvested again at 45½ hours post-irradiation and assayed.

The results are shown in Table 4.

TABLE 4

| UV After or Before Induction | (ergs/cm$^2$) | Interferon Yield* (units/plate) | | |
|---|---|---|---|---|
| | | 0–21½ hr | 21½–45½ hr | Total |
| Control | 0 | 1794 | 102 | 1896 |
| After | 8.8 × 10$^3$ | 4146 | 306 | 4452 |
| Before | 8.8 × 10$^3$ | 5396 | 238 | 5634 |
| After | 2.2 × 10$^4$ | 23038 | 3688 | 26726 |
| Before | 2.2 × 10$^4$ | 24102 | 1102 | 26204 |
| After | 4.4 × 10$^4$ | 26130 | 24178 | 50308 |
| Before | 4.4 × 10$^4$ | 24532 | 5918 | 30450 |

TABLE 4-continued

| UV After or Before Induction | (ergs/cm$^2$) | Interferon Yield* (units/plate) 0–21½ hr | 21½–45½ hr | Total |
|---|---|---|---|---|
| After | 6.6 × 10$^4$ | 24124 | 21258 | 45382 |
| Before | 6.6 × 10$^4$ | 22196 | 5710 | 22767 |
| After | 8.8 × 10 | 21886 | 22250 | 44136 |
| Before | 8.8 × 10 | 5988 | 2484 | 8472 |
| After | 1.3 × 10 | 10792 | 8168 | 18960 |
| Before | 1.3 × 10 | 2298 | 1558 | 3856 |

*Average for 2 plates

Part E — The Effect of Timing of the Ultraviolet Irradiation on the Yields of Interferon Obtained from Human Foreskin Fibroblasts Induced with Polyriboinosinic-polyribocytidylic Acid Complex (poly I:C)

E-1: Human foreskin fibroblasts (HFF), obtained by trypsinization of infant foreskin tissue as described above, are seeded on day 1 on 60 mm. plastic tissue culture plates in 5 ml. MEM-10 growth medium, incubated, and reach confluency on day 3 and are used on day 5. The growth medium is removed and the plates are overlayed with 2 ml. MEM-2A containing 100 mcg./ml. polyriboinosinic-polyribocytidylic acid complex (poly I:C) and incubated for 2 hours. The plates are washed 3 times with saline. Two plates serving as a control are not irradiated and groups of 2 plates each are irradiated immediately [Westinghouse Sterilamp G15T8, 30 cm. working distance, measured dose 45 ergs/mm$^2$/sec. (Blak-Ray Ultraviolet Intensity Meter)] for 15 seconds; or overlayed with 2 ml. MEM-2A, incubated, and irradiated, as above, at various times after induction. After irradiation the plates are overlayed with 2 ml. MEM-2A and incubated. The medium is harvested at 22 hours post-irradiation, assayed, and the plates replenished with 2 ml. fresh MEM-2A and incubated. The medium is harvested again at 45¾ hours post-irradiation and assayed. The results are shown in Table 5.

TABLE 5

| Time UV Treatment Given | Interferon Yield (units/plate)* 22 hr | 45 ¾ hr | Total | % |
|---|---|---|---|---|
| Immediately after induction | 18224 | 15754 | 33978 | 100 |
| 45 min after induction | 6710 | 6558 | 13268 | 39 |
| 140 min after induction | 986 | 348 | 1334 | 3.9 |
| 195 min after induction | 1724 | 214 | 1938 | 5.7 |

TABLE 5-continued

| Time UV Treatment Given | Interferon Yield (units/plate)* 22 hr | 45 ¾ hr | Total | % |
|---|---|---|---|---|
| Control (no UV treatment) | 1516 | 40 | 1556 | 6.0 |

*Average for 2 plates

E-2: Human foreskin fibroblasts (HFF), obtained by trypsinization of infant foreskin tissue as described above, are seeded on day 1 on 60 mm. plastic tissue culture plates in 5 ml. MEM-10 growth medium, incubated, and reach confluency on day 3 and are used on day 5. The growth medium is removed and the plates are overlayed with 2 ml. MEM-2A containing 100 mcg./ml. polyriboinosinic-polyribocytidylic acid complex (poly I:C) and incubated for 2 hours. The plates are washed 3 times with saline. Two plates serving as a control are not irradiated and groups of 2 plates each are irradiated immediately [Westinghouse Sterilamp G15T8, 30 cm. working distance, measured dose 45 ergs/mm$^2$/sec. (Blak-Ray Ultraviolet Intensity Meter)] for 15 seconds; or overlayed with 2 ml. MEM-2A, incubated, and irradiated, as above, at various times after induction. After irradiation the plates are overlayed with 2 ml. MEM-2A and incubated.

The medium is harvested at 7¾ hours post-irradiation, assayed, and the plates replenish with 2 ml. fresh MEM-2A and incubated. The medium is harvested again at 18 hours post-irradiation, assayed, and the plates replenished with 2 ml. fresh MEM-2A and incubated. The medium is again harvested at 45 hours post-irradiation and assayed. The results are shown in Table 6.

TABLE 6

| Time UV Treatment Given | Interferon Yield (units/plate)* 7 ¾ hr | 18 hr | 45 hr | Total | % |
|---|---|---|---|---|---|
| Immediately after induction | 6078 | 6114 | 12228 | 24420 | 100 |
| 30 min after induction | 3108 | 4368 | 8736 | 16212 | 66 |
| 60 min after induction | 1724 | 1858 | 3716 | 7298 | 30 |
| 90 min after induction | 1470 | 1408 | 2816 | 5694 | 23 |
| 120 min after induction | 872 | 962 | 1064 | 2898 | 12 |
| Control (no UV treatment) | 1340 | 472 | <80 | 1812 | 7.4 |

*Average for 2 plates

Part F — The Effect of Ultraviolet Irradiation on the Ability of Human Cell Strain WI-38 to Produce Interferon Human cell strain WI-38 is seeded in growth medium MEM-10 on 60 mm. plastic tissue culture plates, incubated, and used as confluent cell sheets (7 × 10$^5$ cells/plate) after 4 days. The growth medium is removed and two plates overlayed with 2 ml. MEM-2A containing 10 mcg./ml. polyriboinosinic-polyribocytidylic acid complex (poly I:C) and incubated for 2 hours. The cells are washed 3 times with saline. One plate serving as a control is not irradiated and the other plate is irradiated immediately [Westinghouse Sterilamp G15T8, 30 cm. working distance, measured dose 44 ergs/mm$^2$/sec. (Blak-Ray Ultraviolet Intensity Meter)] for 15 seconds.

Control cells are not irradiated. The cells are overlayed with 2 ml. MEM-2A and incubated. The medium from the plates is harvested at 10¾ hours post-irradiation and assayed, and the plates replenished with 2 ml. fresh MEM-2A and incubated. The medium is harvested again 22¾ hours post-irradiation and assayed, and the plates replenished with 2 ml. fresh MEM-2A and incubated. The medium is harvested again 47 hours post-irradiation and assayed.

With another portion of two plates, the growth medium is removed and the plates overlayed with 2 ml. MEM-2A containing 100 mcg./ml. polyriboinosinic-polyribocytidylic acid complex (poly I:C) and incubated for 2 hours. The cells are washed 3 times with saline. One plate serving as a control is not irradiated and the other plate is irradiated immediately [Westinghouse Sterilamp G15T8, 30 cm. working distance, measured dose 44 ergs/mm$^2$/sec. (Blak-Ray Ultraviolet Intensity Meter)] for 15 seconds. Control cells are not irradiated. The cells are overlayed with 2 ml. MEM-2A and incubated. The medium from the plates is harvested at 10¾ hours post-irradiation and assayed, and the plates replenished with 2 ml. fresh MEM-2A and incubated. The medium is harvested again 22¾ hours post-irradiation and assayed, and the plates replenished with 2 ml. fresh MEM-2A and incubated. The medium is harvested again 47 hours post-irradiation and assayed.

The results are shown in Table 7.

TABLE 7

| Sample | Incubation Time | Interferon Yield (units/plate) |
|---|---|---|
| Control | 0–10 ¾ hrs | <20 |
| (10 mcg/ml | 10 ¾–22 ¾ hrs | <20 |
| poly I:C) | 22 ¾–47 hrs | <20 |
| UV Treated | 0–10 ¾ hrs | 224 |
| (10 mcg/ml | 10 ¾–22 ¾ hrs | 440 |
| poly I:C) | 22 ¾–47 hrs | 252 |
| | | 916 |
| Control | 0–10 ¾ hrs | 40 |
| (100 mcg/ml | 10 ¾–22 ¾ hrs | <20 |
| poly I:C) | 22 ¾–47 hrs | <20 |
| UV Treated | 0–10 ¾ hrs | 986 |
| (100 mcg/ml | 10 ¾–22 ¾ hrs | 1668 |
| poly I:C) | 22 ¾–47 hrs | 836 |
| | | 3490 |

EXAMPLE 2

Primary rabbit kidney cells are obtained by trypsinization of kidneys from 350 gm. suckling rabbits as follows:

The tissue is minced with a scalpel and digested 3 times at 37° C. for 15–30 minutes per digestion with 0.25% Bacto trypsin in HBSS. The digests are washed in HBSS one time and pooled in MEM-10. 5 Ml. MEM-10 is used to seed 60 mm. plastic tissue culture plates on day 1 (50 plates per kidney). The plates are fed with MEM-10 on day 3 and used for interferon assay when confluent cell monolayers are obtained (5–8 days). These plates are also used to prepare first passage (p-1) rabbit kidney cells for interferon production as follows:

Primary rabbit kidney cells growing on 60 mm. plastic tissue culture plates are removed by trypsinization and cells from 10 dishes used to seed 24 fresh 60 mm. plastic tissue culture plates in 5 ml. MEM-10. Upon reaching confluency on day 3 the MEM-10 is removed and the plates replenished twice with 5 ml. MEM-2 before use 4 days after reaching confluency.

On day 7 the growth medium is removed and two plates washed 3 times with saline. One plate serving as a control is not irradiated and the other plate is irradiated immediately [Westinghouse Sterilamp G15T8, 30 cm. working distance, measured dose 44 ergs/mm$^2$/sec. (Blak-Ray Ultraviolet Intensity Meter)] for 10 seconds. After irradiation the plates are overlayed with 2 ml. MEM-2A containing 100 mcg./ml. polyriboinosinic-polyribocytidylic acid complex (poly I:C) and incubated for 2 hours. The plates are washed 3 times with saline, given 2 ml. fresh MEM-2A and incubated at 37° C. The medium is harvested at 10¾ hours post-irradiation and titered, the plates replenished with 2 ml. fresh MEM-2A and incubated at 37° C. The medium is again harvested at 22¾ hours post-irradiation and titered.

Another plate on day 5 is overlayed with 2 ml. MEM-2A containing 100 mcg./ml. polyriboinosinic-polyribocytidylic acid complex (poly I:C) after removing the growth medium and then incubated at 37° C. for 2 hours. The plate is washed 3 times with saline. The plate is irradiated immediately [Westinghouse Sterilamp G15T8, 30 cm. working distance, measured dose, 44 ergs/mm$^2$/sec. (Blak-Ray Ultraviolet Intensity Meter)] for 10 seconds. After irradiation the plate is overlayed with 2 ml. MEM-2A and incubated at 37° C. The medium is harvested at 10¾ hours post-irradiation and titered, the plates replenished with 2 ml. fresh MEM-2A and incubated at 37° C. The medium is again harvested at 22¾ hours post-irradiation and titered.

The medium is titered as follows:

Primary rabbit kidney cells obtained by trypsinization of kidneys from 350 gm. suckling rabbits, as described above, are seeded on day 1 on 60 mm. plastic tissue culture plates in 5 ml. MEM-10 growth medium, reach confluency on day 5–8 are used from day 5 to day 8, or when confluent.

The growth medium is removed and the plates are overlayed with 2 ml. Medium 199 (1X) and dilutions of the interferon sample in PBS (pH 7) are added to the plates in a volume of 0.1 to 0.2 ml. Control plates to which are added PBS alone, or an interferon standard in PBS, are also included in the assay. The plates are incubated at 37° C. in a CO$_2$ incubator (5% CO$_2$) for 16–24 hours and then aspirated and challenged with 40–80 pfu of vesicular stomatitis virus in 0.5 ml. HBSS. After 2 hours at 37° C. in a CO$_2$ incubator (5% CO$_2$) the plates are overlayed with 5 ml. Medium 199 plaquing agar. The virus plaques are counted after 3–5 days' incubation at 37° C. in a CO$_2$ incubator (5% CO$_2$).

Interferon concentrations are expressed as the reciprocal of the dilution producing a 50% reduction of virus plaques, as compared to a control without interferon.

One interferon unit is that amount of interferon that produces a 50% reduction of virus plaques, as compared to a control without interferon. In this example, Rabbit Reference Interferon (NIH) is included and, within the accuracy of the assay, the units expressed are equivalent to international units without correction.

The results are shown in Table 8.

TABLE 8

| Dose poly I:C | UV Irradiation* | Time | Interferon Yield (units/ plate) |
|---|---|---|---|
| 100 mcg/ml | (Control) | 0–10 ¾ hrs | 4308 |
| | | 10 ¾– 22 ¾ hrs | 374 |

TABLE 8-continued

| Dose poly I:C | UV Irradiation* | Time | Interferon Yield (units/plate) |
|---|---|---|---|
| 100 mcg/ml | (B) | 0–10 ¾ hrs | 4682 36,632 |
| | | 10 ¾– 22 ¾ hrs | 13,988 |
| | | | 50,620 |
| 100 mcg/ml | (A) | 0–10 ¾ hrs | 44,312 |
| | | 10 ¾– 22 ¾ hrs | 32,496 |
| | | | 76,808 |

*(A) = After induction
(B) = Before induction
(Control) = Not irradiated

EXAMPLE 3

100 mm × 20 mm Falcon plastic tissue culture plates are seeded with 5 × 10⁵ human foreskin fibroblasts (HFF) in 15 ml. MEM-10 growth medium on day 1 and used on day 6 as confluent monolayers. The growth medium is removed and the plates washed once with 4 ml. saline, overlayed with 3 ml. PBS containing 100 mcg./ml. polyriboinosinic-polyribocytidylic acid complex (poly I:C) and incubated at 37° C. (not in 5% $CO_2$ atmosphere) for 1 hour. The plates are washed 2 times with 4 ml. saline and irradiated immediately [Westinghouse Sterilamp G15T8, 30 cm. working distance, measured dose 45 ergs/mm²/sec. (Blak-Ray Ultraviolet Intensity Meter)] for 12 seconds. After irradiation 16 plates (Group A) are overlayed with 4 ml. MEM containing 1.2 mg./ml. sodium bicarbonate, 40 units sodium penicillin G per ml., and 40 mcg. streptomycin phosphate per ml. The plates are incubated at 37° C. under a 5% $CO_2$ atmosphere for 70 hours.

Two plates (Group B) are overlayed with 4 ml. MEM-2A after irradiation.

Three plates (Group C) are overlayed with 4 ml. MEM containing 0.1% rabbit albumin (Sigma, added as a 10% filtered sterilized solution), 1.2 mg./ml. sodium bicarbonate, 50 units sodium penicillin G per ml., and 50 mcg. streptomycin phosphate per ml. After irradiation the plates are incubated at 37° C. under a 5% $CO_2$ atmosphere for 70 hours.

Seventeen plates (Group D) are overlayed with 4 ml. MEM containing 0.1% rabbit albumin (Sigma, added as a 10% filtered sterilized solution), 1.2 mg./ml. sodium bicarbonate, 50 units sodium penicillin G per ml. and 50 mcg. streptomycin phosphate per ml. After irradiation the plates are incubated at 37° C. under a 5% $CO_2$ atmosphere for 4 hours. The medium is removed and the plates are overlayed with 4 ml. MEM containing 1.2 mg./ml. sodium bicarbonate, 50 units sodium penicillin G per ml., and 50 mcg. streptomycin phosphate per ml. The plates are incubated at 37° C. under a 5% $CO_2$ atmosphere for 66 hours.

The medium for each group is harvested at 70 hours and assayed for interferon in the manner described in Example 1. The results are shown in Table 9.

TABLE 9

| Group | Interferon Yield (units/plate) at 70 hours |
|---|---|
| A | 70,483[1] |
| B | 74,746[2] |
| C | 73,465[3] |

TABLE 9-continued

| Group | Interferon Yield (units/plate) at 70 hours |
|---|---|
| D | 82,600[4] |

[1]Average for 15 plates
[2]Average for 2 plates
[3]Average for 3 plates
[4]Average for 17 plates

EXAMPLE 4

The term "PBS containing DEAE-poly I:C complex" as used herein means:

A mixture of poly I:C (10 mcg./ml.) and diethylaminoethyl (DEAE)-dextran (100 mcg./ml.) prepared as follows:

A 10 mg./ml. filter sterilized stock solution of DEAE-dextran (Pharmacia; molecular weight, 2 × 10⁶) in PBS is diluted in 3 volumes PBS and 1 volume of 1 mg./ml. stock solution of poly I:C in saline is added while the mixture is stirred. The mixture (DEAE-poly I:C complex) is incubated at 37° C. (not in a $CO_2$ incubator) for 30 minutes before use. Before exposing to cells the DEAE-poly I:C complex is diluted 1/20 in PBS.

Human foreskin fibroblasts (HFF), obtained by trypsinization of infant foreskin tissue, are seeded on day 1 on 60 mm plastic tissue culture plates in 5 ml. MEM-10 growth medium, incubated, and used on day 5 as confluent monolayers. The growth medium is removed and the plates are overlayed with 2 ml. PBS containing DEAE-poly I:C complex and incubated for 1 hour. The plates are washed twice with saline. Two plates (Group A) serving as a control are not irradiated and groups of 2 plates each (Group B, C, and D) are irradiated immediately (Westinghouse Sterilamp G15T8, 30 cm. working distance) for 1, 5 and 10 seconds, respectively. After irradiation the plates are overlayed with 2 ml. MEM-2A and incubated for 24 hours. The medium is harvested and assayed for interferon in the manner described in Example 1. The plates are replenished with 2 ml. fresh MEM-2A and incubated for 24 hours. The medium is harvested again at 48 hours post-irradiation and assayed for interferon in the manner described in Example 1. The results are shown in Table 10.

TABLE 10

| | UV Exposure | Interferon Yield* (units/plate) | | |
|---|---|---|---|---|
| | | 0–24 hr | 24–48 hr | Total |
| Group A | 0 seconds | 2652 | 878 | 3530 |
| Group B | 1 second | 4224 | 874 | 5098 |
| Group C | 5 seconds | 6026 | 1014 | 7040 |
| Group D | 10 seconds | 2744 | 1746 | 4490 |

*Average for 2 plates

EXAMPLE 5

The term "MEM-2A containing DEAE-poly I:C complex" as used herein means:

A mixture of poly I:C (10 mcg./ml.) and diethylaminoethyl (DEAE-dextran (100 mcg./ml.) prepared as follows:

A 10 mg./ml. filter sterilized stock solution of DEAE-dextran (Pharmacia; molecular weight, 2 × 10⁶) in PBS is diluted in 3 volumes PBS and 1 volume of 1 mg./ml. stock solution of poly I:C in saline is added while the mixture is stirred. The mixture (DEAE-poly I:C complex) is incubated at 37° C. (not in a $CO_2$ incubator) for 30 minutes before use. Before exposing to cells the DEAE-poly I:C complex is diluted 1/20 in MEM-2A.

Human foreskin fibroblasts (HFF), obtained by trypsinization of infant foreskin tissue, are seeded on day 1 on 60 mm. plastic tissue culture plates in 5 ml. MEM-10 growth medium, incubated, and used on day 5 as confluent cell sheets containing approximately $6 \times 10^5$ cells/plate. The growth medium is removed from 3 plates and the plates are overlayed with 2 ml. MEM-2A containing DEAE-poly I:C complex and incubated for 2 hours. The plates are washed 3 times with saline. One plate serving as a control is not irradiated and the remaining 2 plates are irradiated immediately [Westinghouse Sterilamp G15T8, 30 cm. working distance, measured dose 50 ergs/$mm^2$/sec. (Blak-Ray Ultraviolet Intensity Meter)] for 15 seconds. After irradiation the plates are overlayed with 2 ml. MEM-2A and incubated for 7¾ hours. The medium is harvested and assayed for interferon in the manner described in Example 1. The plates are replenished with 2 ml. fresh MEM-2A and incubated for 8¼ hours. The medium is harvested again at 16 hours post-irradiation and assayed for interferon. The plates are replenished with 2 ml. fresh MEM-2A and incubated for 13½ hours. The medium is harvested again at 29½ hours post-irradiation and assayed for interferon. The plates are replenished with 2 ml. fresh MEM-2A and incubated for 13½ hours. The medium is harvested again at 43 hours post-irradiation and assayed for interferon.

In a process as described above, the results shown in Table 11 were obtained.

TABLE 11

| Sample | Incubation Time | Interferon Yield (units/plate) |
|---|---|---|
| Control (DEAE-poly I:C complex) | 0–7 ¾ hrs | 1888 |
| | 7 ¾–16 hrs | 1110 |
| | 16–29 ½ hrs | 560 |
| | 29 ½–43 hrs | <80 |
| | TOTAL | 3558 |
| UV Treated (DEAE-poly I:C complex) | 0–7 ¾ hrs | 1606 |
| | 7 ¾–16 hrs | 620 |
| | 16–29 ½ hrs | 752 |
| | 29 ½–43 hrs | 296 |
| | TOTAL | 3274 |

EXAMPLE 6

Part A

Human foreskin fibroblasts (HFF), obtained by trypsinization of infant foreskin tissue, are seeded on day 1 on 60 mm. plastic tissue culture plates in 5 ml. MEM-10 growth medium, incubated, and used on day 6 as confluent cell sheets. The growth medium is removed from 6 plates and the plates washed 3 times with saline. One plate serving as a control is not irradiated and the remaining 5 plates each are irradiated immediately (Westinghouse Sterilamp G15T8, 30 cm. working distance) for 1, 5, 10, 20 and 60 seconds, respectively. After irradiation the plates are overlayed with 5 ml. MEM-10 and incubated for 18 hours. The medium from the plates is removed and the plates are overlayed with 2 ml. MEM-2A containing 10 mcg./ml. polyriboinosinic-polyribocytidylic acid complex (poly I:C) and incubated for 2 hours. The plates are washed 3 times with saline, overlayed with 2 ml. fresh MEM-2A and incubated 13 hours. The medium is harvested and assayed for interferon in the manner described in Example 1. The results are shown in Table 12.

TABLE 12

| UV Exposure | Interferon Yield* (units/plate) |
|---|---|
| 0 seconds | 40.8 |
| 1 second | 27.8 |
| 5 seconds | 97.8 |
| 10 seconds | 186.6 |
| 20 seconds | 34.0 |
| 60 seconds | 23.2 |

*Average for 2 plates

Part B

Human foreskin fibroblasts (HFF), obtained by trypsinization of infant foreskin tissue, are seeded on day 1 on 60 mm. plastic tissue culture plates in 5 ml. MEM-10 growth medium, incubated, and used on day 7 as confluent cell sheets. The growth medium is removed from 10 plates and the plates washed 3 times with saline. Two plates serving as a control are not irradiated and groups of two plates each are irradiated immediately (Westinghouse Sterilamp G15T8, 30 cm. working distance) for 1, 5, 10, and 15 seconds, respectively. After irradiation the plates are overlayed with 5 ml. MEM-10 and incubated for 18 hours. The medium from the plates is removed and the plates are overlayed with 1.4 ml. PBS containing DEAE-poly I:C complex (DEAE-poly I:C complex prepared in the manner described in Example 4) and incubated for 2 hours. The plates are washed 3 times with HBSS, overlayed with 2 ml. fresh MEM-2A and incubated 14 hours. The medium is harvested and assayed for interferon in the manner described in Example 1.

In a process as described above, the results shown in Table 13 were obtained.

TABLE 13

| UV Exposure | Interferon Yield* (units/plate) |
|---|---|
| 0 seconds | 8686 |
| 1 second | 7736 |
| 5 seconds | 5202 |
| 10 seconds | 2280 |
| 15 seconds | 248 |

*Average for 2 plates

I claim:
1. In the method of producing interferon in vitro which consists of inducing interferon-producing human or animal cells with an inducing-effective amount of a non-viral interferon inducer, the improvement comprising irradiating the cells with from about 50 ergs/$mm^2$ to about 2500 ergs/$mm^2$ of ultraviolet irradiation applied at a point in time during the time span of from 8 hours prior to until about 4 hours subsequent to, including concurrent with, the addition of the non-viral interferon inducer.

2. The method of claim 1 in which the non-viral interferon inducer is a polynucleotide.

3. The method of claim 2 in which the polynucleotide is polyriboinosinic-polyribocytidylic acid complex.

4. The method of claim 3 in which the cells are irradiated subsequent to the addition of the polyriboinosinic-polyribocytidylic acid complex.

5. The method of claim 4 in which the cells are irradiated with from about 100 ergs/mm$^2$ to about 1000 ergs/mm$^2$.

6. The method of claim 5 in which the cells are human fibroblast cells.

7. The method of claim 5 in which the cells are rabbit kidney cells.

8. The method of claim 6 in which the human fibroblast cells are human foreskin fibroblast cells.

9. The method of claim 3 in which the cells are irradiated concurrent with the addition of the polyriboinosinic-polyribocytidylic acid complex.

10. The method of claim 9 in which the cells are irradiated with from about 100 ergs/mm$^2$ to about 1000 ergs/mm$^2$.

11. The method of claim 10 in which the cells are human fibroblast cells.

12. The method of claim 10 in which the cells are rabbit kidney cells.

13. The method of claim 11 in which the human fibroblast cells are human foreskin fibroblast cells.

14. The method of claim 3 in which the cells are irradiated prior to the addition of the polyriboinosinic-polyribocytidylic acid complex.

15. The method of claim 14 in which the cells are irradiated with from about 100 ergs/mm$^2$ to about 1000 ergs/mm$^2$.

16. The method of claim 15 in which the cells are human fibroblast cells.

17. The method of claim 15 in which the cells are rabbit kidney cells.

18. The method of claim 16 in which the human fibroblast cells are human foreskin fibroblast cells.

19. The method of claim 1 in which the cells are irradiated with from about 100 ergs/mm$^2$ to about 1000 ergs/mm$^2$.

20. The method of claim 1 in which the cells are irradiated at a point in time during the time span of immediately prior to until 2 hours subsequent to the addition of the non-viral interferon inducer.

21. The method of claim 20 in which the cells are irradiated with from about 100 ergs/mm$^2$ to about 1000 ergs/mm$^2$.

22. The method of claim 21 in which the non-viral interferon inducer is polyriboinosinic-polyribocytidylic acid complex.

* * * * *

UNITED STATES PATENT OFFICE
CERTIFICATE OF CORRECTION

Patent No. 4,007,086            Dated February 8, 1977

Inventor(s) Ramon D. Hamilton

It is certified that error appears in the above-identified patent and that said Letters Patent are hereby corrected as shown below:

Column 3, line 53:   "2537 A." should read -- 2537 $\overset{\circ}{A}$. --.
Column 4, line 25:   "Earle's" should read -- (Earle's --.
Column 6, line 39:   "Bacto trypsin." should read -- Bacto® trypsin. --.
Column 6, line 49:   "2537 A" should read -- 2537 $\overset{\circ}{A}_®$ --.
Column 6, line 55:   "Falcon" should read -- Falcon® --.
Column 6, lines 62-63:   "tryspinization" should read -- trypsinization --.
Column 7, line 32:   "tryspin" should read -- trypsin --.
Column 7, line 37:   "tryspin" should read -- trypsin --.
Column 8, lines 64-65:   "typsinization" should read -- trypsinization --.
Column 9, line 54:   "MEM:2A" should read -- MEM-2A --.
Column 10, line 25:   "5 MEM-10" should read -- 5 ml. MEM-10 --.
Column 13, line 54:   "Bacto trypsin" should read -- Bacto® trypsin --.
Column 15, line 19:   "Falcon plastic" should read -- Falcon® plastic --.

Signed and Sealed this

Twenty-eighth Day of July 1981

[SEAL]

Attest:

GERALD J. MOSSINGHOFF

Attesting Officer      Commissioner of Patents and Trademarks